(12) United States Patent
Deuel et al.

(10) Patent No.: US 12,127,736 B2
(45) Date of Patent: Oct. 29, 2024

(54) CONTROL MECHANISM FOR END EFFECTORS AND METHOD OF USE

(71) Applicant: Boston Scientific Scimed, Inc., Maple Grove, MN (US)

(72) Inventors: Christopher R. Deuel, Melrose, MA (US); Ramon Estevez, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/358,405

(22) Filed: Jul. 25, 2023

(65) Prior Publication Data

US 2023/0363750 A1    Nov. 16, 2023

Related U.S. Application Data

(63) Continuation of application No. 17/645,529, filed on Dec. 22, 2021, now Pat. No. 11,744,567.

(Continued)

(51) Int. Cl.
| | |
|---|---|
| *A61B 17/072* | (2006.01) |
| *A61B 17/00* | (2006.01) |
| *A61B 17/068* | (2006.01) |
| *A61B 17/04* | (2006.01) |
| *A61B 17/115* | (2006.01) |

(Continued)

(52) U.S. Cl.
CPC ...... *A61B 17/00234* (2013.01); *A61B 17/068* (2013.01); *A61B 17/07207* (2013.01); *A61B 17/0469* (2013.01); *A61B 17/072* (2013.01); *A61B 2017/07214* (2013.01); *A61B 17/115* (2013.01); *A61B 17/1285* (2013.01); *A61B 2017/2927* (2013.01); *A61B 34/30* (2016.02); *A61B 34/71* (2016.02)

(58) Field of Classification Search
CPC .............. A61B 17/068; A61B 17/0469; A61B 17/00234; A61B 17/072; A61B 17/07207; A61B 17/115; A61B 17/1285; A61B 2017/00477; A61B 2017/07214; A61B 2017/2927; A61B 2017/2946; A61B 34/30; A61B 34/71
USPC ..... 227/19, 175.1, 175.2, 176.1; 606/1, 139, 606/219
See application file for complete search history.

(56) References Cited

U.S. PATENT DOCUMENTS

| | | |
|---|---|---|
| 5,354,311 A | 10/1994 | Kambin et al. |
| 6,645,196 B1 | 11/2003 | Nixon et al. |

(Continued)

*Primary Examiner* — Scott A Smith
(74) *Attorney, Agent, or Firm* — Bookoff McAndrews, PLLC

(57) ABSTRACT

A medical device including an attachment device having a longitudinal axis, a pivot arm having a first end pivotally attached to the attachment device, an end effector pivotally attached to a second end of the pivot arm and configured to move from a first configuration to a second configuration, and a longitudinally extending body attached to a proximal end of the end effector. Movement of the longitudinally extending body in a proximal direction rotates the end effector from the first configuration to the second configuration, the end effector is approximately parallel to the longitudinal axis of the attachment device in the first configuration, and the end effector is angled relative to the longitudinal axis of the attachment device in the second configuration.

20 Claims, 4 Drawing Sheets

Related U.S. Application Data

(60) Provisional application No. 63/131,197, filed on Dec. 28, 2020.

(51) Int. Cl.
*A61B 17/128* (2006.01)
*A61B 17/29* (2006.01)
*A61B 34/00* (2016.01)
*A61B 34/30* (2016.01)

(56) References Cited

U.S. PATENT DOCUMENTS

| | | |
|---|---|---|
| 7,725,214 B2 | 5/2010 | Diolaiti |
| 8,490,851 B2 | 7/2013 | Blier et al. |
| 8,562,592 B2 | 10/2013 | Conlon et al. |
| 8,672,209 B2 | 3/2014 | Crainich |
| 8,784,435 B2 | 7/2014 | Cooper et al. |
| 10,743,851 B2 | 8/2020 | Swayze et al. |
| 10,806,448 B2 * | 10/2020 | Shelton, IV ..... A61B 17/07207 |
| 10,856,870 B2 | 12/2020 | Harris et al. |
| 10,959,771 B2 | 3/2021 | Boudreaux et al. |
| 11,744,567 B2 * | 9/2023 | Deuel ................. A61B 17/068 227/175.1 |
| 2011/0071555 A1 | 3/2011 | McBrayer et al. |
| 2014/0076955 A1 | 3/2014 | Lorenz |
| 2015/0150620 A1 | 6/2015 | Miyamoto et al. |
| 2017/0224330 A1 | 8/2017 | Worthington et al. |
| 2020/0054320 A1 | 2/2020 | Harris et al. |
| 2020/0275925 A1 | 9/2020 | Smith et al. |
| 2020/0315617 A1 | 10/2020 | Nicholas et al. |

* cited by examiner

CONTROL MECHANISM FOR END EFFECTORS AND METHOD OF USE

CROSS-REFERENCE TO RELATED APPLICATIONS

This application is a continuation of U.S. Patent Application No. 17/645,529, filed Dec. 22, 2021, now U.S. Pat. No. 11,744,567, which claims the benefit of priority of U.S. Provisional Patent Application No. 63/131,197, filed Dec. 28, 2020, each of which is incorporated herein by reference in its entirety.

TECHNICAL FIELD

This disclosure relates to minimally invasive (e.g., endoscopic and/or laparoscopic) medical devices and related methods of use. In embodiments, the disclosure relates to one or more control mechanisms for end effectors, e.g., tissue fastening devices such as stapler devices, and related methods of use, among other aspects.

BACKGROUND

Technological developments have given users of medical systems, devices, and methods, the ability to conduct increasingly complex procedures on subjects. The coupling of tissue in, for example, a subject's gastrointestinal tract or other locations within the body, is a type of procedure in which difficulties may arise. Surgical devices that grasp or clamp tissue between opposing jaw structures and then join the tissue by surgical fasteners are known. The fasteners may include surgical staples. In some procedures, a cutting instrument may be provided to cut the tissue which has been joined by the fasteners. Drawbacks of these systems may include, for example, the fact that they have to access target sites via tortuous paths and/or paths having small cross-sectional diameters. This may result in not being able to properly access target sites to staple and/or cut tissue using scopes, which may increase therapy time and/or cost, and/or result in trauma to the patient (e.g., if more invasive procedures are required to access the target site). This disclosure may address one or more of these problems or other problems in the art. The scope of the disclosure, however, is defined by the attached claims and not the ability to address a specific problem.

SUMMARY OF THE DISCLOSURE

According to an aspect, a medical device includes an attachment device having a longitudinal axis, a pivot arm having a first end pivotally attached to the attachment device, an end effector pivotally attached to a second end of the pivot arm and configured to move from a first configuration to a second configuration, and a longitudinally extending body attached to a proximal end of the end effector, wherein movement of the longitudinally extending body in a proximal direction is configured to rotate the end effector from the first configuration to the second configuration, and wherein the end effector is approximately parallel to the longitudinal axis of the attachment device in the first configuration, and wherein the end effector is angled relative to the longitudinal axis of the attachment device in the second configuration.

Movement of the longitudinally extending body in a distal direction may be configured to cause the end effector to move in the distal direction.

Movement of the longitudinally extending body in the distal direction may be configured to cause the pivot arm to pivot relative to the distal end of the attachment device.

The medical device may further include a locking mechanism to move from a locked position to an unlocked position, wherein the locking mechanism may be configured to prevent pivotal movement of the end effector when the locking mechanism is in the locked position.

The locking mechanism may be biased in the locked position by a spring.

The medical device may further include a locking wire extending from the locking mechanism in the proximal direction, wherein the locking mechanism may be configured to move from the locked position to the unlocked position in response to a force on the locking wire in the proximal direction sufficient to overcome a spring force.

The locking mechanism may include a locking slot located on the pivot arm and a pawl.

An angle defined by the end effector and the longitudinal axis in the second configuration may be is equal to or greater than 20 degrees and less than or equal to 50 degrees.

Movement of the longitudinally extending body in the direction may be configured to move the second end of the pivot arm radially outward from the longitudinal axis.

The attachment mechanism has a proximal end that may be configured to attach to a distal end of a catheter.

The longitudinally extending body may extend along an outer surface of the catheter from the end effector to a proximal end of the catheter.

The attachment mechanism may include a proximal body and a pair of spaced apart arms extending distally from the proximal body, wherein each of the pair of arms may include an opening, wherein each opening may be configured to receive a pivot arm pin fixing the pivot arm to the attachment mechanism, and a first pivot axis may be defined about the pivot arm pins.

A first protrusion may extend from an inner surface of a first arm from the pair of arms toward the longitudinal axis, wherein a second protrusion may extend from a second arm from the pair of arms toward the longitudinal axis, wherein the pivot arm may include a pair of openings configured to mate to the first and second protrusions, and wherein contact of the pair of openings with the first and second protrusions may define a proximalmost movement of the pivot arm.

The end effector may include a pair of jaws pivotally connected to one another, wherein an actuation wire may be operably connected to at least one jaw of the pair of jaws and may extend from the end effector to a proximal end of the medical device through a lumen of the longitudinally extending body, and wherein actuation of the actuation wire may be configured to cause the pair of jaws to pivot relative to each other.

The pivot arm may include a pair of openings at the second end, wherein each opening may be configured to receive an end effector pin fixing the end effector to the pivot arm, and wherein a second pivot axis may be defined about the end effector pins.

According to another aspect, a medical device includes a catheter having a longitudinal axis, an attachment mechanism coupled to a distal end of a catheter, a pivot arm pivotally connected, at a first end of the pivot arm, to the attachment mechanism and configured to rotate about a first pivot axis, an end effector pivotally connected at a second end of the pivot arm and configured to rotate about a second pivot axis, and a longitudinally extending body configured to move in a proximal direction and a distal direction, wherein movement of the longitudinally extending body is configured to pivot the pivot arm about the first and the second axes.

The end effector may be configured to move between a first configuration, in which the end effector may be approximately parallel to the longitudinal axis of the catheter, and a second configuration, in which the end effector may be angled relative to the longitudinal axis of the catheter.

The second end of the pivot arm and a distal end of the end effector may be configured to extend along parallel axes when the longitudinally extending body is in the first configuration, and wherein the second end of the pivot arm and the distal end of the end effector may be configured to extend in radially opposite directions when the longitudinally extending body is in the second configuration.

According to yet another aspect, a medical method includes advancing an end effector of a medical device to a target site within a patient, wherein the end effector is attached to a distal end of a catheter by an attachment device, and wherein the end effector is positioned in an in-line orientation such that the end effector is parallel to a longitudinal axis of the catheter, actuating a longitudinally extending body connected to a proximal end of the end effector to cause the end effector to move from the in-line orientation to an active orientation, wherein the end effector is angled relative to the longitudinal axis of the catheter in the active orientation, positioning an object between a first jaw and a second jaw of the end effector via a medical tool extending from a distal end of the catheter, and actuating a control mechanism to cause the first jaw to pivot relative to the second jaw and perform a procedure on the tissue.

The method may further include moving a locking wire in a proximal direction to disconnect a locking mechanism, allowing the end effector to move from the active orientation, rotating the end effector from the active orientation to the in-line orientation, and removing the end effector from the patient.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figures 1A, 1B:
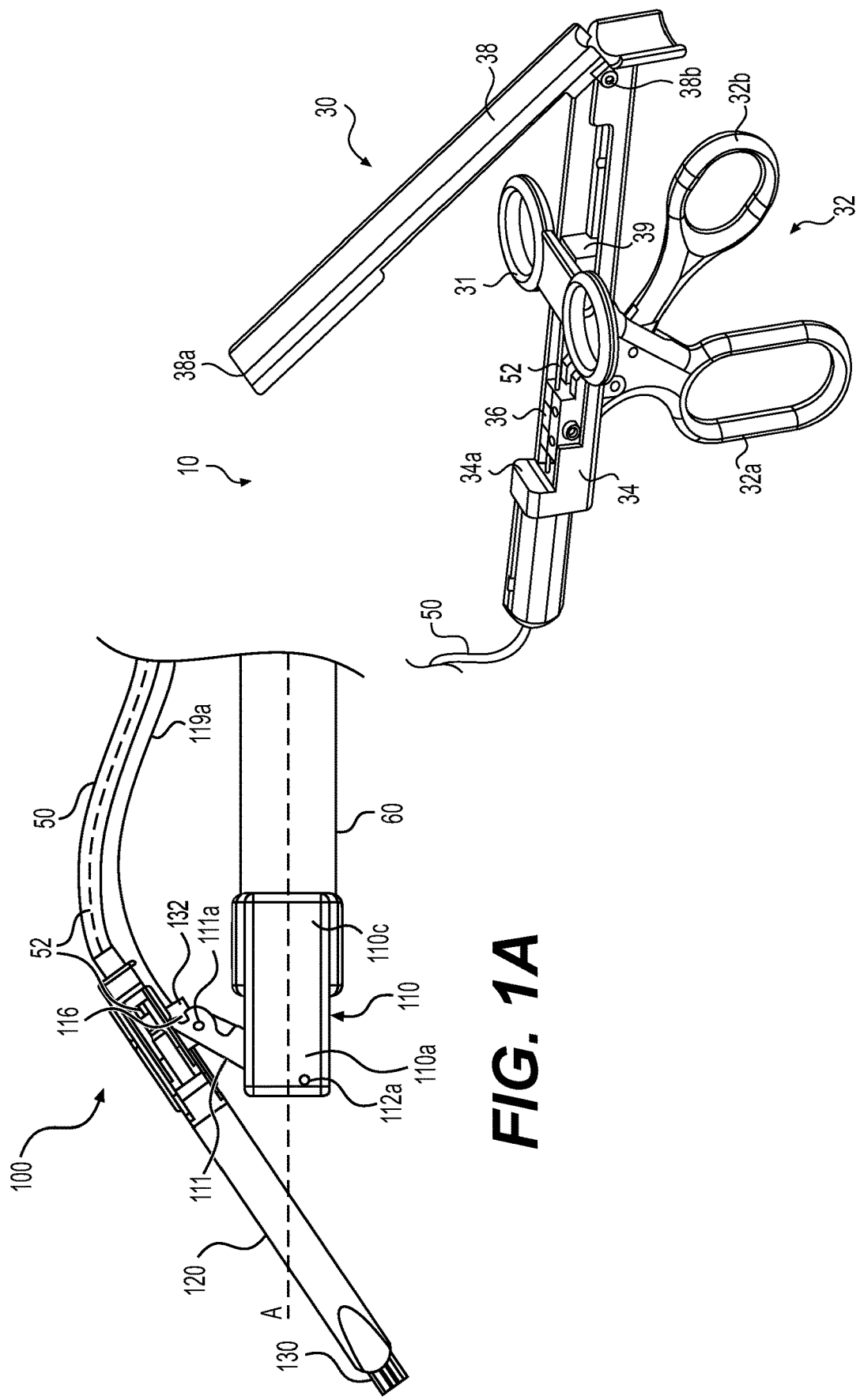
FIG. 1A is an enlarged schematic view of a distal end of a medical device including an end effector.
FIG. 1B is a perspective view of a proximal end of the medical device, according to an embodiment.

This disclosure is described with reference to exemplary medical systems and medical tools for accessing a target site, for example, for grasping, cutting, and/or stapling tissue, and providing a control mechanism for controlling an orientation of an end effector relative to the medical tools. This may provide improved medical tool functionality and/or may assist medical professionals to improve access to target sites, which may improve cutting and/or fastening of tissue. However, it should be noted that reference to any particular device and/or any particular procedure is provided only for convenience and is not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Additionally, terms that indicate the geometric shape of a component/surface refer to exact and approximate shapes.

Embodiments of this disclosure may be used to fasten tissue in an endo-luminal space, or facilitate the process thereof. According to an example, the fastening device may be a tissue stapling apparatus, which may include a resection or cutting mechanism (e.g., an integrated knife) and a stapling mechanism (e.g., a stapler). The fastening device may be delivered through an endoscope working channel to the target tissue site. Alternatively, the fastening device may be attached to a distal end of the endoscope. All or parts of the fastening device could be metallic (such as stainless steel, titanium, or cobalt chrome), plastic (such as polyetheretherketone (PEEK) or the like), or include a shape memory metal (such as Nitinol), a shape memory polymer, a polymer, or any combination of materials.

While reference is made herein to a fastening device with a control mechanism for controlling an orientation of the fastening device, the described control mechanism may be used with any set of jaws or other end effectors pivotally connected together at a distal end of a catheter, sheath, tube, or the like. The control mechanism may enable pivotal movement of the end effector about one or more pivot points at the distal end of an endoscope, which may provide improved grasping of tissues. For example, the control mechanism may enable the end effector to be arranged parallel to or in line with a longitudinal axis of the endoscope during insertion of the end effector to the target site, and may enable the end effector to rotate about one or more pivot points and change positions to grasp tissue once the end effector is at the target site. In this manner, the end effector and the endoscope may navigate tortuous pathways within the body.

FIGS. 1A and 1B show a distal portion and a proximal portion of an apparatus 10, respectively, in accordance with an example of this disclosure. Apparatus 10 may include a scope (e.g., a colonoscope, endoscope, duodenoscope, or the like) and a medical device including an end effector (e.g., an end effector 100 in FIG. 1A). The scope may be used for imaging, providing light to a target site, and/or for introducing instruments to the target site, and a surgical stapling apparatus configured to engage body tissue and apply a plurality of fasteners thereto during minimally invasive procedures, such as those procedures using the scope. In some embodiments, the device including the end effector may be a suturing apparatus to deliver a suture for tissue closure during minimally invasive surgical procedures. Apparatus 10 may be used to apply a suture, clips, or other fasteners, but will be primarily discussed in the context of grasping tissue in preparation of performing additional procedures to the tissue, e.g., stapling and/or cutting the tissue.

As illustrated in FIGS. 1A and 1B, the grasping or stapling device of apparatus 10 may include a handle assembly 30 at a proximal end, an end effector 100 at a distal end, and a longitudinally extending body 50 (e.g., a shaft, a catheter, or the like) connecting a distal end of handle assembly 30 to a proximal end of end effector 100. Longitudinally extending body 50 may extend any length suitable for endoscopic or laparoscopic procedures. In some instances, longitudinally extending body 50 may be configured to be positioned within a working channel of an endoscope. Alternatively, longitudinally extending body 50 may extend along an outer surface of the endoscope if, for example, the endoscope includes only a single lumen and/or a diameter of the lumen(s) of the endoscope are too small to receive longitudinally extending body 50. In some instances, longitudinally extending body 50 and end effector 100 are located on the outer surface of the endoscope to reduce the cross-sectional area of the endoscope used in conjunction with apparatus 10, which may enable apparatus 10 to maneuver along tortuous paths and access the target site.

Longitudinally extending body 50 may be detachable from handle assembly 30 to facilitate insertion of longitudinally extending body 50 into a working channel of an endoscope or a channel of another device, for example by backloading longitudinally extending body 50 into the working channel. In some examples, longitudinally extending body 50 may be flexible, steerable, and/or may be rotatable about its axis. Longitudinally extending body 50 may include a lumen (or multiple lumens) for positioning actuation wires within (e.g., an actuation wire 52), for actuating end effector 100 via handle assembly 30 or actuating any other portion of apparatus 10. Longitudinally extending body 50 may be configured to receive a plurality of actuation wires or a single actuation wire. In some examples, longitudinally extending body 50 may be fixedly coupled to end effector 100, and in other examples longitudinally extending body 50 may be removably or releasably coupled to end effector 100. Unless stated otherwise, any wire or actuation device described herein may extend from handle assembly 30 to end effector 100 via a lumen of longitudinally extending body 50. Alternatively, or additionally, one or more of these actuation wires or devices (e.g., a wire 119a) may extend from handle assembly 30 to end effector 100 outside of (e.g., adjacent to) longitudinally extending body 50.

Longitudinally extending body 50 of apparatus 10 may be inserted into or mounted on a catheter 60 of an endoscope, and end effector 100 may be positioned relative to catheter 60, as shown in FIG. 1A, and discussed further herein. Catheter 60 may be the central shaft of a scope (e.g., a colonoscope, endoscope, duodenoscope, or the like). Catheter 60 may include one or more central lumens through which medical tools, imaging cables, and/or illumination cables may extend. The imaging cables and the illumination cables may connect to and may control imaging and light emitting devices, respectively, at a distal end of catheter 60. Medical tools, such as grasping tools, or apparatus 10 itself, may be inserted into and extend through one or more lumens of catheter 60 and may extend distally of a distalmost end of catheter 60. One or more medical tools may be used to grasp tissue at a target site and/or to perform a medical procedure on tissue at the target site. These tools may be used in conjunction with apparatus 10.

The endoscope handle may include actuators, including knobs and/or buttons, to control the medical tools, imaging devices, and light emitting devices. Ports or other openings at the endoscope handle or at a proximal end of catheter 60 may provide access to the one or more lumens of catheter 60, and may allow the medical tools or other devices to be introduced into these lumens. Handle assembly 30 of apparatus 10 may be operated by a user in conjunction with the endoscope handle and/or may be positioned relative to the endoscope handle.

Handle assembly 30 of apparatus 10 may include a handle 32 and a body 34. Handle 32 may include a fixed portion 32a and an actuator portion 32b. Fixed portion 32a of handle 32 may be fixedly coupled to body 34. Actuator portion 32b may include a circular or oval portion or ring for positioning a user's finger within, which may assist a user in holding handle assembly 30. In some examples, actuator portion 32b of handle 32 may be an actuator, which may be pivotally coupled to body 34 and movable relative to fixed portion 32a of handle 32. In some examples, actuator portion 32b of handle 32 may be coupled to a proximal portion of an actuation wire, such as an actuation wire 52, via an adjustable coupler 36, as will be described herein. In other examples, actuator portion 32b of handle 32 may be configured to control any other mechanism of apparatus 10, such as actuation of the deployment of staples from end effector 100 or the like. It will be understood that actuation wire 52 may have sufficient rigidity to be pushed in the distal direction and pulled in the proximal direction.

In some examples, handle assembly 30 may include a moveable cover 38 pivotally coupled to housing 34 at pivot point 38b. In FIG. 1B, cover 38 is shown in an open position, exposing the internal portions of body 34. Cover 38 may be coupled to a proximal portion of body 34 and may cover the internal components of handle assembly 30 when positioned in a closed configuration, e.g., when a distalmost end 38a of cover 38 is positioned adjacent a surface 34a of body 34. Cover 38 may be positioned to cover the internal components of body 34 (e.g., in a closed configuration) via a coupling mechanism at a distal portion of cover 38 and a distal portion of handle assembly 30, such as a snap-fit mechanism or the like. When in the closed configuration, cover 38 may form a pair of slots (not shown) in cooperation with body 34. When the distal portion of cover 38 is uncoupled from the distal portion of body 34, a user may rotate or pivot cover 38 at pivot point 38b in order to access to the internal components of handle assembly 30.

Handle assembly 30 may include one or more adjustable couplers 36, 39, which may be configured to receive a portion of an actuation wire, such as actuation wire 52. Any of adjustable couplers 36, 39 may be a vice which is moveable in order to clamp down onto actuation wire 52 and fixedly couple actuation wire 52 to the adjustable couplers 36, 39. In some examples, adjustable couplers 36, 39 may be moveable via a screw to adjust couplers 36, 39 and couple or uncouple actuation wire 52 from couplers 36, 39 or adjust the tension of actuation wire 52. Couplers 36, 39 may be used in the movement of additional wires described herein.

Adjustable coupler 39 may be coupled to a longitudinal actuator 31 and may be moveable longitudinally via translating longitudinal actuator 31 along body 34. Longitudinal actuator 31 may be partially positioned within housing 34 and may be slidable longitudinally within the two slots formed when cover 38 is positioned over the internal components of handle assembly 30 in a closed configuration.

Longitudinal actuator 31 may include a pair of opposing circular or oval portions or rings, with each circular portion defining an aperture for a user to position one or more fingers within. In some examples, longitudinal actuator 31 may be coupled to actuation wire 52, such as via adjustable coupler 39 or via a different coupler within body 34, and may be configured to control staple deployment from end effector 100. In other examples, longitudinal actuator 31 may be configured to control any other mechanism of apparatus 10, such as proximal/distal movement of actuation wire 52 or the like. Alternatively, two actuators may be used, a first actuator for actuating a cutting device and a second actuator for actuating a stapling device. Handle assembly 30 is but one example of an actuation device of end effector 100, and any other handle assembly suitable for actuating end effector 100 may be used.

End effector 100 may include a pair of jaws, e.g., anvil 120 and a body 130 of a stapler device (shown also in FIG. 4), which may be coupled to the distal end of catheter 60 via an attachment device 110. For example, attachment device 110 may be connected at the distal end of longitudinally extending body 50 and may attach a proximal end of end effector 100 to longitudinally extending body 50 via an adhesive, laser welding, or the like. The attachment between the proximal end of attachment device 110 and the distal end of longitudinally extending body 50 may be sufficient to receive forces in the distal and the proximal directions such that end effector 100 may pivot about one or more axes and/or may move in the distal and the proximal directions, as will be described herein. An actuator and/or a distal end of one of the jaws, e.g., anvil 120, may also be attached to a distal end of actuation wire 52. In this manner, anvil 120 and/or body 130 of end effector 100 may be actuated via longitudinal actuator 31.

Figure 2:
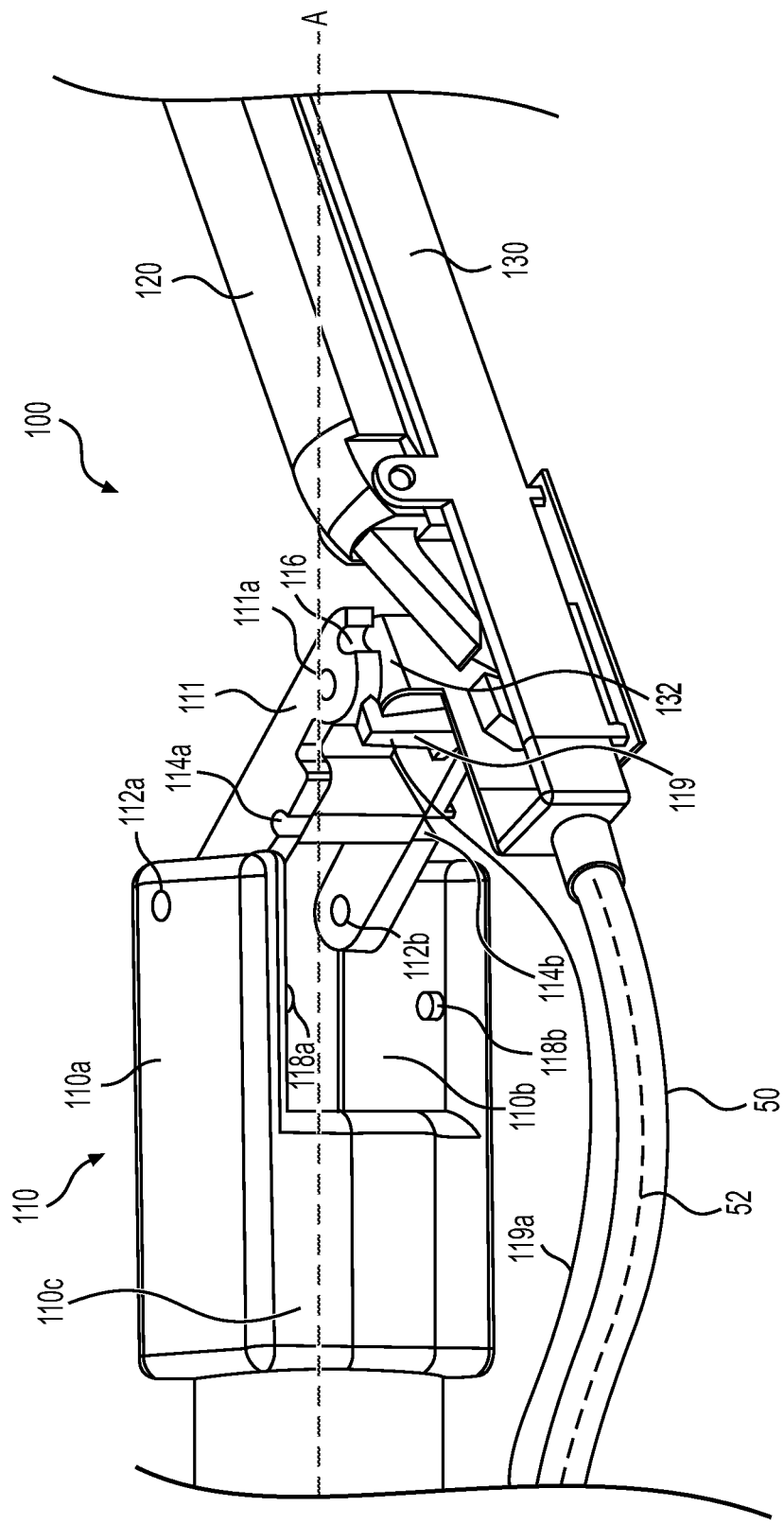
FIG. 2 is a perspective view of a pivot arm and the end effector of the medical device of FIG. 1A, according to an embodiment.

With reference to FIGS. 1 and 2, a pivot arm 111 may be pivotally attached to end effector 100 via one or more pins 111*a* (pins 111*a* may define a pivot axis) (although only one pin 111*a* is shown in the figures, it is contemplated that multiple pins 111 may be included, e.g., to increase the range of motion). One or more protrusions 132 may extend from the side of end effector 100 (for example, from a side of body 130) and may receive pin 111*a* through pinholes (not shown) in protrusions 132, thereby fixing pins 111*a* relative to protrusions 132. Pins 111*a* define a pivot axis of pivot arm 111 and end effector 100. Pins 111*a* may also be received in an opening (not shown) at a distal end of pivot arm 111 (FIG. 2), which may fix pivot arm 111 to protrusions 132 about a pivot axis, and which may allow end effector 100 to pivot relative to pivot arm 111.

Pivot arm 111 may also include openings (not shown) at a proximal end. The openings may be connected to a distal end of attachment mechanism 110. For example, one or more pins 112*a*, 112*b* (pins 112*a*, 112*b* may define a pivot axis) may connect openings in the proximal end of pivot arm 111 to corresponding openings in the distal end of attachment mechanism 110. Pins 112*a*, 112*b* may secure or fix pivot arm 111 to attachment mechanism 110 via a pivot axis. Since pins 112*a*, 112*b* define a pivot axis, pivot arm 111 may pivot relative to attachment mechanism 110.

Figure 3:
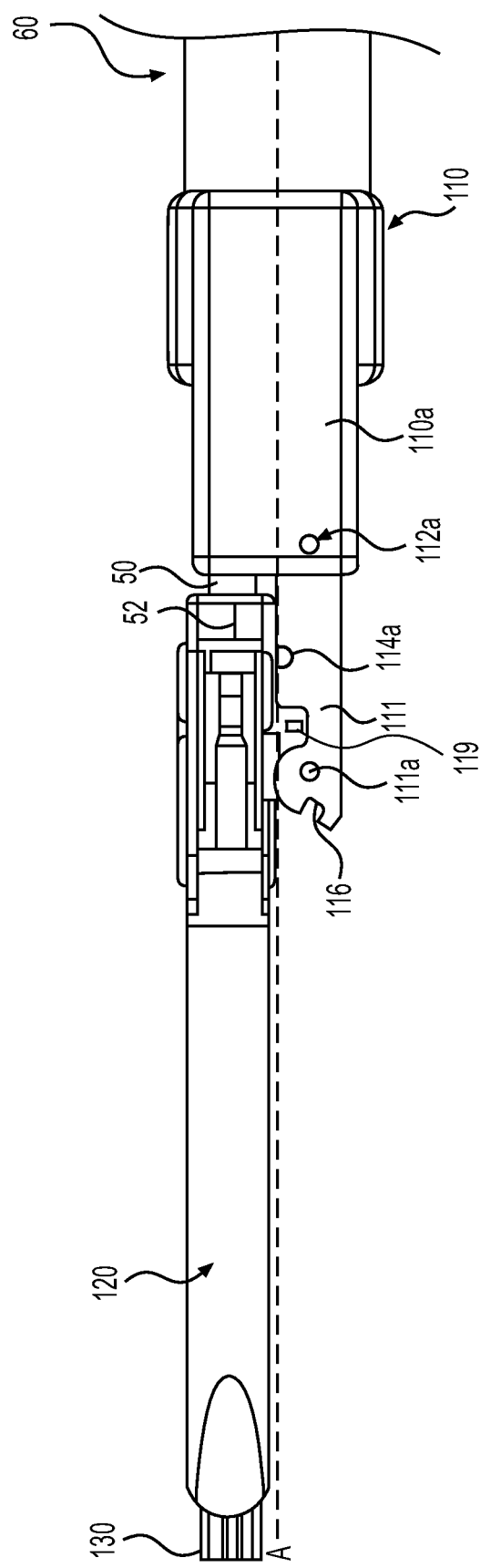
FIG. 3 is a top view of the pivot arm and the end effector of FIG. 2, according to an embodiment.

Referring to FIGS. 2 and 3, pivot arm 111 includes recesses 114*a*, 114*b* located on top and bottom supports of pivot arm 111. Recesses 114*a*, 114*b* each form a partial circular in shape, but are not limited thereto. Recesses 114*a*, 114*b* on attachment mechanism 110 to provide a stop mechanism for pivot arm 111 in the proximal direction. As will be described herein, pivot arm 111 may rotate about pins 112*a*, 112*b* until recesses 114*a*, 114*b* contact protrusions 118*a*, 118*b*, preventing further rotation of pivot arm 111 in the proximal direction.

Figure 4:
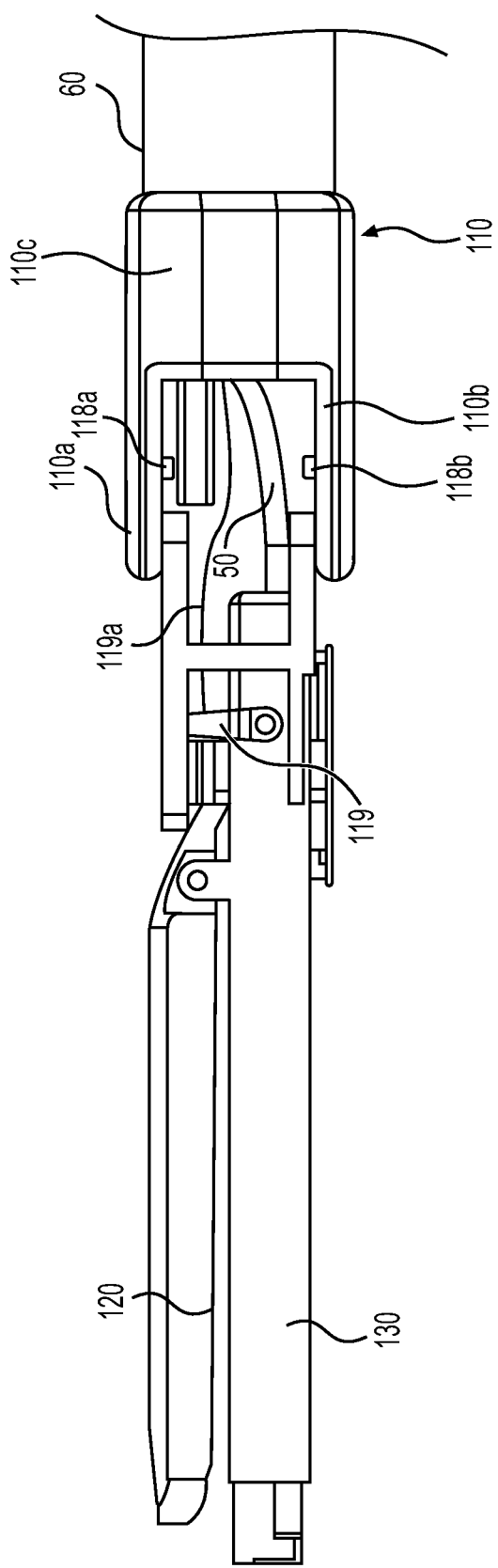
FIG. 4 is a side view of the pivot arm and the end effector of FIG. 2, according to an embodiment.

Pivot arm 111 may also include an opening 116 in a surface of pivot arm 111, shown in the orientation depicted in FIG. 2 as the topmost surface of pivot arm 111, although it is understood that this orientation may change as catheter 60 and end effector 100 are maneuvered during use. Opening 116 may receive and may cooperate with a locking mechanism 119, e.g., a pawl, to maintain a position of pivot arm 111 when pivot arm 111 is angled relative to a longitudinal axis A of catheter 60 (FIGS. 1-3). Locking mechanism 119 may be pivotally attached to body 130 of end effector 100, or may be pivotally attached to protrusion arm 132 of end effector 100 (FIG. 4). Locking mechanism 119 may include a spring (not shown) or other biasing member to bias or urge locking mechanism 119 in a closed position, e.g., toward opening 116. As pivot arm 111 rotates about pivot axes defined by pins 111*a* and 112*a*, 112*b*, locking mechanism 119 may be urged into opening 116, e.g., a locking slot, when locking mechanism 119 and opening 116 are aligned. Locking mechanism 119 may prevent rotational movement of end effector 100 and/or pivot arm 111 when locking mechanism 119 is disposed within and locked to opening 116.

Wire 119*a* may be attached to locking mechanism 119 and may be pulled in a proximal direction to overcome the spring force and to disconnect locking mechanism 119 from opening 116, thereby allowing rotational movement of end effector 100 and/or pivot arm 111. It will also be understood that a user may move wire 119*a* in the distal direction to move locking mechanism 119 into opening 116 and lock the relative movement of pivot arm 111 and/or end effector 100 about the rotational axes defined by pins 111*a* and 112*a*, 112*b*. It will be understood that pivot arm 111 may include a plurality of openings 116 to enable a user to lock pivot arm 111 at multiple angles relative to longitudinal axis A of catheter 60. For example, pivot arm 111 may include two, three, or more openings 116, the position of each opening 116 defining an angle of end effector 100 relative to longitudinal axis A. for example, the angle formed by end effector 100 and longitudinal axis A may be between 0 degrees and 90 degrees, approximately 20 degrees to approximately 50 degrees, or approximately 45 degrees.

Attachment device 110, as shown in FIG. 2, may include a body 110*c* defining an aperture at a proximal end and walls 110*a*, 110*b* extending from a distal end of body 110*c* creating a U-shaped opening. An inner wall of body 110*c* defining the aperture of attachment device 110 may have a diameter larger than a diameter of an outer surface of catheter 60 of the endoscope. In this manner, attachment device 110 may slide onto the distal end of catheter 60 and may be removably or permanently attached via an adhesive, laser welding, screw thread, or the like. Further, medical tools, an imaging device, and/or a light emitting device attached to or extending from catheter 60 may access the target site via the aperture of attachment device 110. Alternatively, it will be understood that the outer wall of the proximal end of attachment device 110 may have a diameter smaller than an inner wall of catheter 60, such that attachment device 110 is configured to slide into the lumen of catheter 60 and removably or permanently attach to catheter 60 using adhesive, laser welding, screw thread, or the like.

As described herein, protrusions 118*a*, 118*b* extend from inner surfaces of walls 110*a*, 110*b* of attachment device 110 toward longitudinal axis A (FIG. 2). In some aspects, protrusions 118*a*, 118*b* may prevent rotational movement of pivot arm 111 once pivot arm 111 reaches a predetermined maximum angle of rotation relative to longitudinal axis A of catheter 60 (e.g., approximately 90 degrees).

Pivot arm 111 and end effector 100 may move from a first position (e.g., an in-line position) (FIG. 3), in which at least portions of pivot arm 111 and/or end effector 130 extend distally of the distalmost end of catheter 60 and are each approximately parallel to longitudinal axis A, to a second position. The second position (e.g., an angled position) (FIG. 1) may be achieved when at least portions of pivot arm 111 and/or end effector 130 are moved in a proximal direction by rotating pivot arm 111 and/or end effector 130 about the axes defined by pins 111a and/or 112a, 112b.

A method of operating apparatus 10 will now be described. Apparatus 10 may be introduced to a body via a natural orifice (e.g., the mouth or the anus) or via an incision or other medically induced opening. End effector 100 may be advanced to a target site within the body, e.g., by pushing distally on catheter 60 and/or longitudinally extending body 50. End effector 100 may be advanced along with catheter 60 in a closed configuration, e.g., a configuration in which end effector 100 is parallel to longitudinal axis A of catheter 60, which may enable end effector 100 and catheter 60 to have a narrower profile and thus to more easily navigate one or more tortuous paths within the body.

Once end effector 100 reaches the target site within the body, the angle of end effector 100 relative to longitudinal axis A may be adjusted. For example, the user may move longitudinally extending body 50 in the proximal direction, which may cause end effector 100 to rotate about the pivot axis defined by pin(s) 111a and/or may cause pivot arm 111 to rotate about the pivot axis defined by pins 112a, 112b. As the user moves longitudinally extending body 50 in the proximal direction, the distal end of end effector 100 may move toward and/or may cross over longitudinal axis A, such that a middle portion of end effector 100 is positioned along longitudinal axis A (FIG. 1). As end effector 100 rotates, a distal end of pivot arm 111 may also move radially outward, e.g., away from longitudinal axis A, and in the proximal direction. As end effector 100 is rotated from the in-line position (first position) to the working position (second position), locking mechanism 119 may be urged or biased into opening 116 to lock end effector 100 in the desired working position. Alternatively, or additionally, the user may move wire 119a in the distal direction, which may cause locking mechanism 119 to move into opening 116. It will be understood that while the operation is described as being performed with locking mechanism 119, it is not necessary to lock end effector 100 in a position before actuating anvil 120 and body 130 of end effector 100.

Once the locking mechanism 119 is moved into opening 116, the user may move actuation wire 52 in the proximal and the distal directions to pivot anvil 120 relative to body 130 and grasp tissue, staple tissue, and/or perform other medical procedures to the tissue at the target site. The user may also use any tools, imaging devices, and/or light emitting devices associated with catheter 60. During the medical procedure, the user may change an angle of end effector 100 relative to longitudinal axis A. In some instances, changing the angle of end effector 100 relative to longitudinal axis A may require the user to move wire 119a proximally to cause locking mechanism 119 to be disconnected from opening 116. Once locking mechanism 119 is moved from opening 116, the user may move longitudinally extending body 50 proximally and distally to change the angle of end effector 100 relative to longitudinal axis A. Once the desired angle is achieved, the position of end effector 100 may be locked by pushing wire 119a distally and/or allowing the biasing member to move locking mechanism 119 into the one or more openings 116, as described herein.

Once the medical procedure is performed, apparatus 10 may be removed from the body. Wire 119a may be moved in the proximal direction, thereby moving locking mechanism 119 from opening 116. The user may then push longitudinally extending body 50 in the distal direction, such that end effector 100 and pivot arm 111 approach the in-line orientation. Once end effector 100 and pivot arm 111 achieve the in-line orientation, apparatus 10 may be removed from the body by pulling proximally on catheter 60. In some instances, a user may apply a force in the distal direction on longitudinally extending body 50 during removal of apparatus 10 to ensure end effector 100 and pivot arm 111 maintain the in-line orientation. Alternatively, a locking mechanism (such as locking mechanism 119) may maintain the in-line position of end effector 100 and pivot arm 111 during removal.

While exemplary medical systems have been described, it will be understood that the particular arrangements of elements in these fastening systems are not limited. Moreover, a size, a shape, and/or the materials of the fastening systems are not limited. As described herein, there is included a control mechanism for controlling a position of an end effector relative to a longitudinal axis of a scope. Performing various medical procedures may be improved by enabling a user to insert the end effector in an in-line orientation, thereby reducing a size of the device, and to move to the end effector to an operation position to perform one or more medical operations using the end effector.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   an attachment device having a longitudinal axis;
   a pivot arm having a first end pivotally attached to the attachment device;
   an end effector pivotally attached to a second end of the pivot arm and configured to transition from a first configuration to a second configuration; and
   a shaft attached to a proximal end of the end effector,
   wherein movement of the shaft is configured to transition the end effector from the first configuration to the second configuration.

2. The medical device of claim 1, wherein the movement of the shaft in a distal direction is configured to cause the pivot arm to pivot relative to a distal end of the attachment device.

3. The medical device of claim 2, wherein movement of the shaft in a distal direction is configured to move the second end of the pivot arm radially outward from the longitudinal axis.

4. The medical device of claim 1, wherein the attachment device, has a proximal end that is configured to attach to a distal end of a catheter.

5. The medical device of claim 1, wherein the shaft extends along an outer surface of a catheter from the end effector to a proximal end of the catheter.

6. The medical device of claim 1, wherein the shaft is configured to be positioned within a working channel of an endoscope, and wherein the shaft comprises a lumen configured to receive at least an actuation wire.

7. A medical device, comprising:
an attachment device coupled to a distal end of a catheter;
a pivot arm pivotally connected, at a first end of the pivot arm, to the attachment device, wherein the first end of the pivot arm is configured to rotate about a first pivot axis;
an end effector pivotally connected to a second end of the pivot arm and configured to rotate about a second pivot axis;
wherein at least a first and a second protrusion extend from the attachment device toward a longitudinal axis of the attachment device;
wherein the pivot arm includes at least a first opening and a second opening configured to mate with the first and the second protrusions, respectively; and
wherein contact of the first and the second openings with the first and the second protrusions defines a proximal most movement of the pivot arm.

8. The medical device of claim 7, wherein the end effector further includes at least one pin that is received within a third opening the pivot arm, and wherein the second pivot axis is defined by the at least one pin.

9. The medical device of claim 7, wherein the attachment device includes a proximal body and a pair of spaced apart arms extending distally from the proximal body, wherein each of the pair of arms includes an opening, wherein each opening is configured to receive a respective pin of a pair of pins attaching the pivot arm to the attachment device, and the first pivot axis is defined by the pair of pins.

10. The medical device of claim 7, wherein the first opening and the second opening each have a shape that is a partial circle.

11. The medical device of claim 7, wherein the first opening is on a first support of the pivot arm, and wherein the second opening is on a second support of the pivot arm.

12. The medical device of claim 11, wherein the first opening is on a side surface of the first support, and wherein the second opening is on a side surface of the second support.

13. The medical device of claim 7, wherein the attachment device includes a first wall and a second wall opposite to the first wall, wherein the first protrusion is disposed on the first wall, and wherein the second protrusion is disposed on the second wall.

14. The medical device of claim 7, wherein the pivot arm includes a third opening on a distal surface of the pivot arm, and wherein the end effector includes a locking mechanism configured to be received within the third opening in at least some configurations of the end effector.

15. The medical device of claim 14, wherein the locking mechanism is received within the third opening in a configuration in which the end effector is angled with respect to a longitudinal axis of the attachment device.

16. A medical device, comprising:
an attachment device, having a longitudinal axis;
a pivot arm having a first end pivotally attached to the attachment device;
an end effector pivotally attached to a second end of the pivot arm, wherein the end effector includes a pair of jaws pivotally connected to one another; and
a shaft attached to a proximal end of the end effector, wherein an actuation wire is operably connected to at least one jaw of the pair of jaws and extends from the end effector to a proximal end of the medical device through a lumen of the shaft, and wherein actuation of the actuation wire is configured to cause the pair of jaws to pivot relative to each other,
wherein longitudinal movement of the shaft is configured to transition the end effector from a first configuration to a second configuration.

17. The medical device of claim 16, wherein the attachment device further comprises a body at a proximal end, wherein a plurality of walls extend from the body.

18. The medical device of claim 16, wherein the end effector further comprises a locking mechanism configured to move from a locked position to an unlocked position, wherein the locking mechanism is configured to prevent pivotal movement of the end effector when the locking mechanism is in the locked position.

19. The medical device of claim 18, further comprising a locking wire extending from the locking mechanism in a proximal direction, wherein the locking mechanism is configured to move from the locked position to the unlocked position in response to a proximal force on the locking wire.

20. The medical device of claim 18, wherein the locking mechanism is biased in the locked position by a spring, and wherein the pivot arm includes a locking slot for receiving the locking mechanism in the locked position.

* * * * *